(12) United States Patent
Karlson et al.

(10) Patent No.: US 9,056,142 B2
(45) Date of Patent: Jun. 16, 2015

(54) ISOTOPE PRODUCTION METHOD

(75) Inventors: Jan Roger Karlson, Oslo (NO); Peer Børretzen, Nærsnes (NO)

(73) Assignee: Algeta ASA, Oslo (NO)

( * ) Notice: Subject to any disclaimer, the term of this patent is extended or adjusted under 35 U.S.C. 154(b) by 0 days.

(21) Appl. No.: 13/695,355

(22) PCT Filed: Apr. 29, 2011

(86) PCT No.: PCT/EP2011/002156
§ 371 (c)(1),
(2), (4) Date: Jan. 3, 2013

(87) PCT Pub. No.: WO2011/134672
PCT Pub. Date: Nov. 3, 2011

(65) Prior Publication Data
US 2013/0095031 A1    Apr. 18, 2013

(30) Foreign Application Priority Data

Apr. 30, 2010  (GB) .................................. 1007353.4

(51) Int. Cl.
| | | |
|---|---|---|
| A61K 51/00 | (2006.01) | |
| A61K 51/02 | (2006.01) | |
| A61K 51/12 | (2006.01) | |
| G21G 1/00 | (2006.01) | |

(52) U.S. Cl.
CPC ............ A61K 51/00 (2013.01); A61K 51/1282 (2013.01); G21G 1/0005 (2013.01); *G21G 2001/0042* (2013.01)

(58) Field of Classification Search
USPC ........... 424/1.11, 1.13, 1.21, 1.25, 1.29, 1.33, 424/1.37, 1.41, 1.45, 1.49, 1.53, 1.57, 1.61, 424/1.69, 1.73
See application file for complete search history.

(56) References Cited

U.S. PATENT DOCUMENTS

| | | |
|---|---|---|
| 4,390,517 A | 6/1983 | O'Brien et al. |
| 5,809,394 A | 9/1998 | Bray et al. |
| 5,885,465 A | 3/1999 | Bray et al. |
| 6,635,234 B1 * | 10/2003 | Larsen et al. ................. 424/1.11 |
| 7,553,461 B2 | 6/2009 | Horwitz et al. |
| 2003/0206857 A1 | 11/2003 | Larsen et al. |
| 2007/0009409 A1 | 1/2007 | Gali et al. |
| 2007/0131618 A1 | 6/2007 | Horwitz et al. |

OTHER PUBLICATIONS

B.Zielinska et al. An Improved method for the production of Ac-225/Bi213 from Th-229 for targeted alpha therapy, Solvent Extraction and Ion Exchange, 25, 339-349, 2007.*
Howell et al., "Radiotoxicity of Gadolinium-148 and Radium-223 in Mouse Testes: Relative Biological Effectiveness of Alpha-Particle Emitters In Vivo," Radiation Research 147: 342-348 (1997).
International Search Report for PCT/EP2011/002156, mailed Jul. 25, 2011 (4 pages).
Written Opinion of the International Searching Authority for PCT/EP2011/002156, mailed Jul. 25, 2011 (4 pages).
Guseva et al., "Anion-exchange separation of radium from alkaline-earth metal actinides in aqueous-methanol solution of $HNO_3$, $^{227}Ac$-$^{223}Ra$ Generator," Radiochemistry. 46(1):58-62 (2004).
Office Action from U.S. Appl. No. 13/695,353, dated Dec. 16, 2013 (9 pages).
First Examination Report for New Zealand Patent Application No. 700258, dated Oct. 10, 2014 (2 pages).
Henriksen et al., "$^{223}Ra$ for endoradiotherapeutic applications prepared from an immobilized $^{227}Ac/^{227}Th$ source," Radiochimica Acta 89.661-666 (2001).

* cited by examiner

Primary Examiner — Michael G Hartley
Assistant Examiner — Jagadishwar Samala
(74) Attorney, Agent, or Firm — Clark & Elbing LLP

(57) ABSTRACT

The present invention relates to a method for the generation of $^{223}Ra$ of pharmaceutically tolerable purity comprising: i) preparing a generator mixture comprising $^{227}Ac$, $^{227}Th$ and $^{223}Ra$ in a first aqueous solution comprising a first mineral acid; ii) loading said generator mixture onto a DGA separation medium (e.g. resin); iii) eluting said $^{223}Ra$ from said DGA separation medium using a second mineral acid in a second aqueous solution to give an eluted $^{223}Ra$ solution; and iv) stripping the DGA separation medium of said $^{227}Ac$ and $^{227}Th$ by flowing a third mineral acid in a third aqueous solution through the DGA separation medium in a reversed direction; The invention further relates to high purity radium-223 formed or formable by such a method as well as pharmaceutical compositions comprising such radium-223 of pharmaceutical purity.

17 Claims, 6 Drawing Sheets

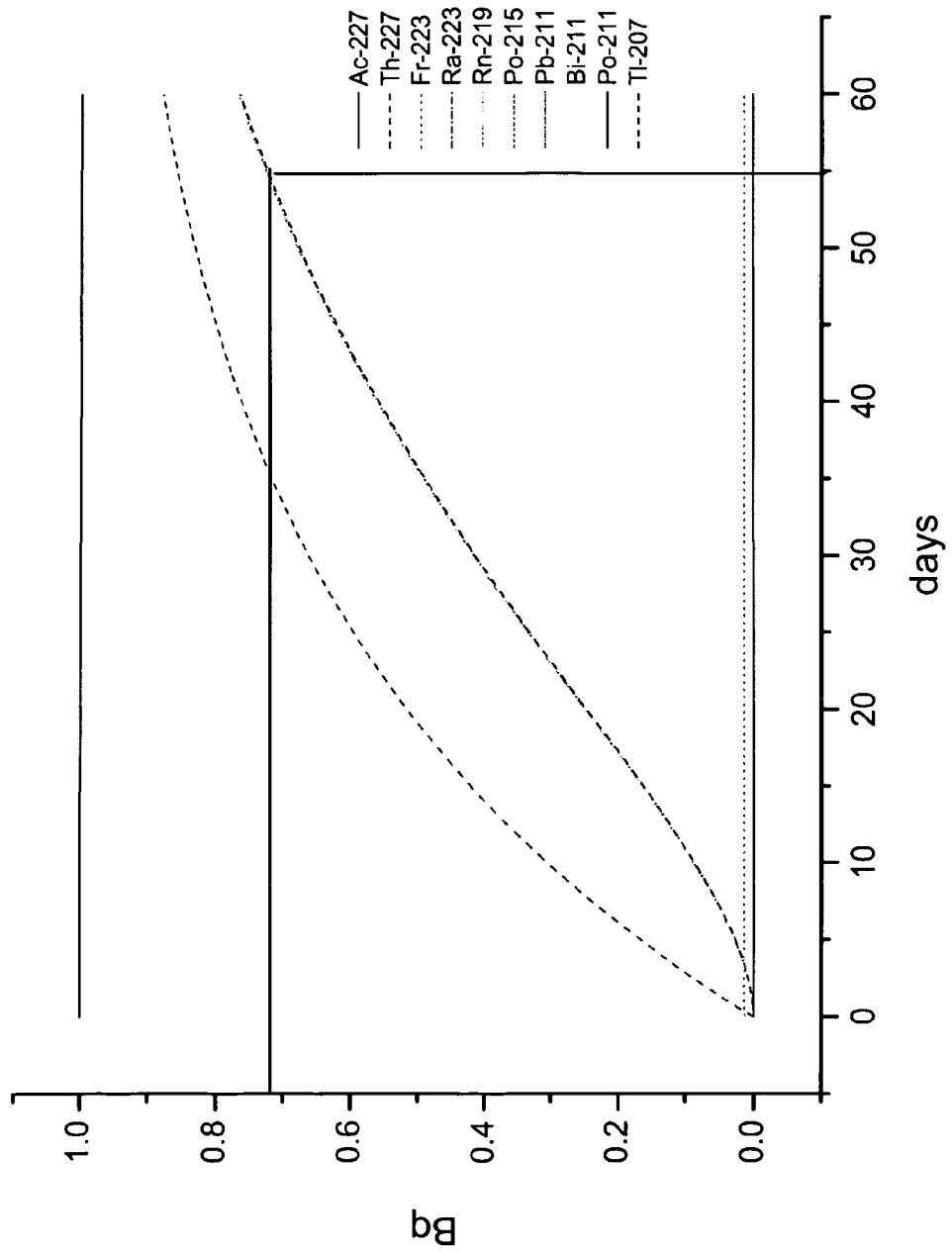
Figure 1 Ingrowth of $^{227}$Th and $^{223}$Ra into $^{227}$Ac. The vertical line mark the time needed to have 72 % ingrowth of $^{223}$Ra.

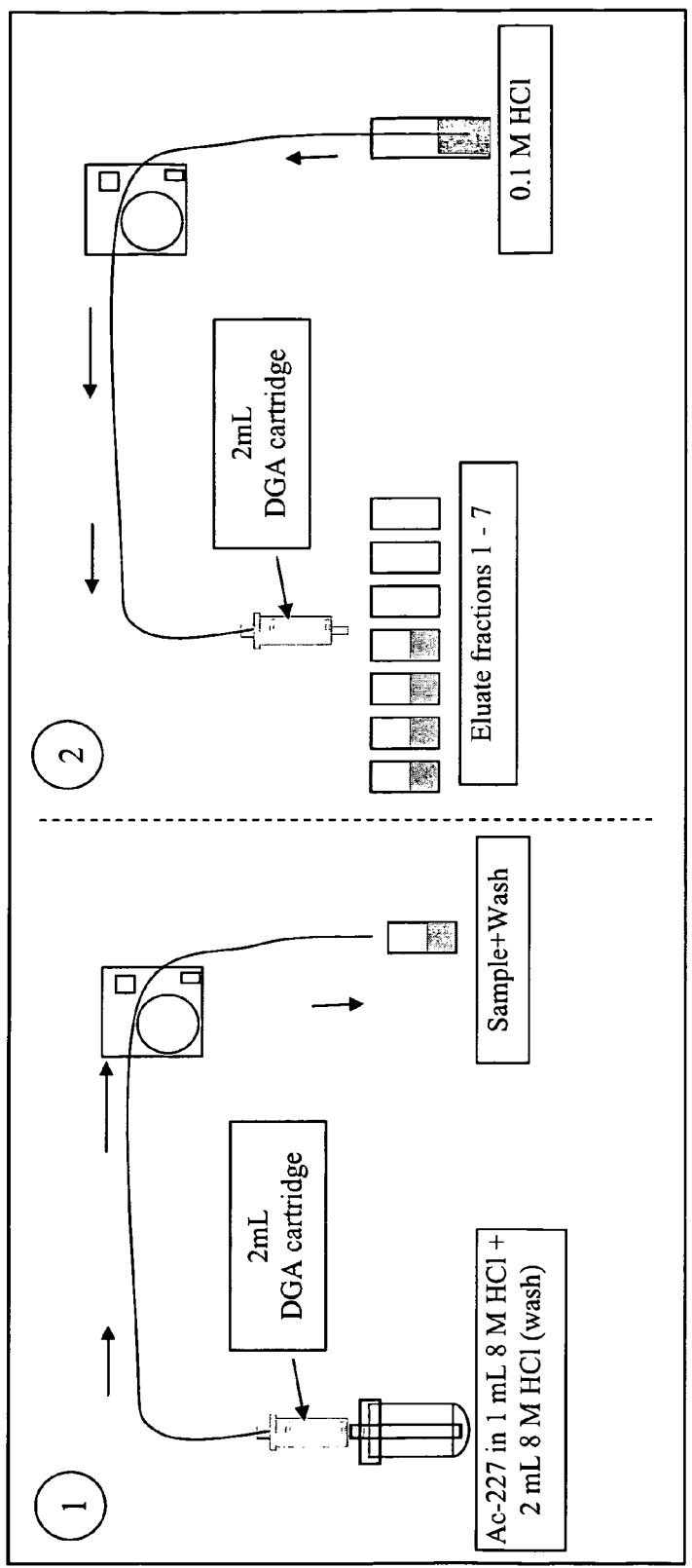
Figure 2 Experimental setup for DGA resin experiment 1

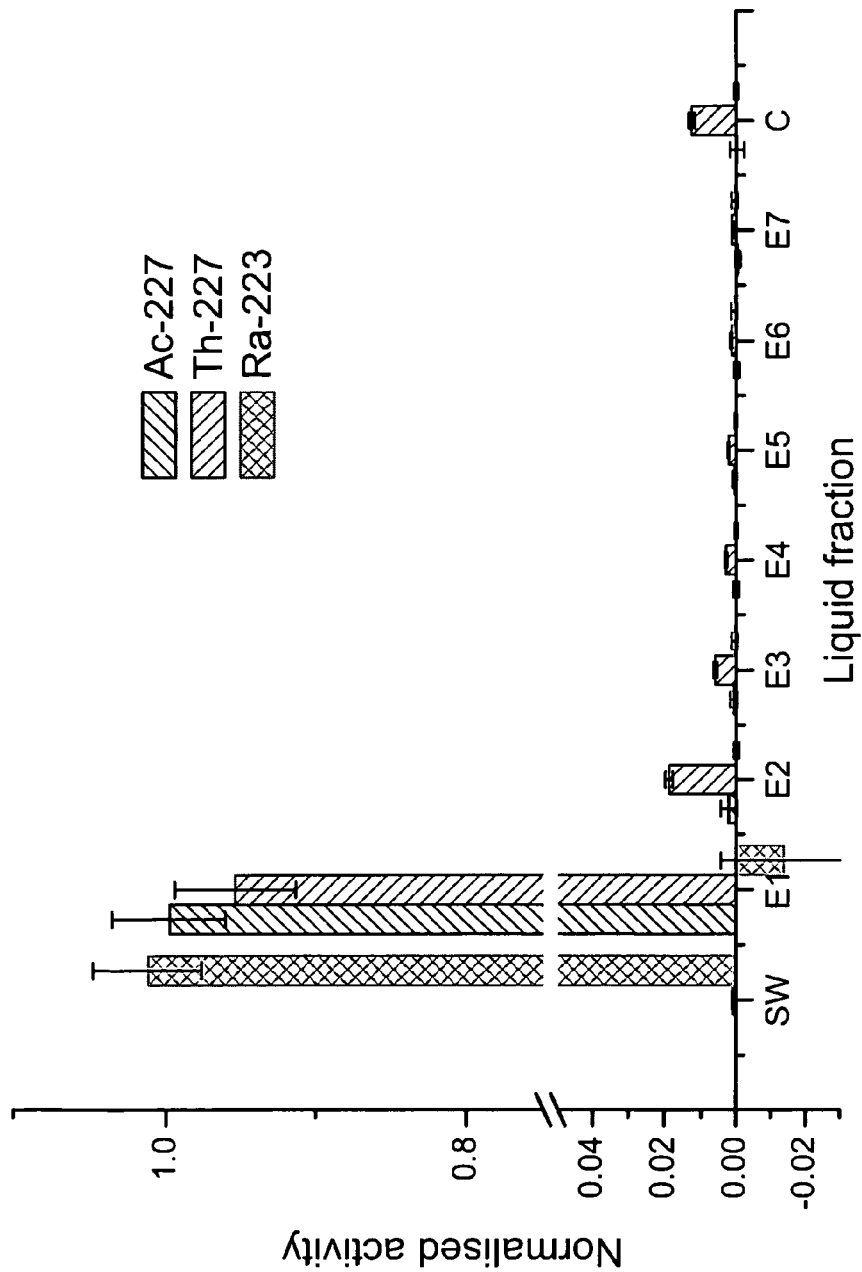
Figure 3 Normalised activity of $^{227}$Ac, $^{227}$Th and $^{223}$Ra in various fractions in the DGA-branched resin after elution. Error bars show 3 s.d. counting uncertainty. Legend: SW: sample + wash fraction (8 M HCl), E1-E7: elution fraction 1-7 (0.1 M HCl), C: cartridge after elution.

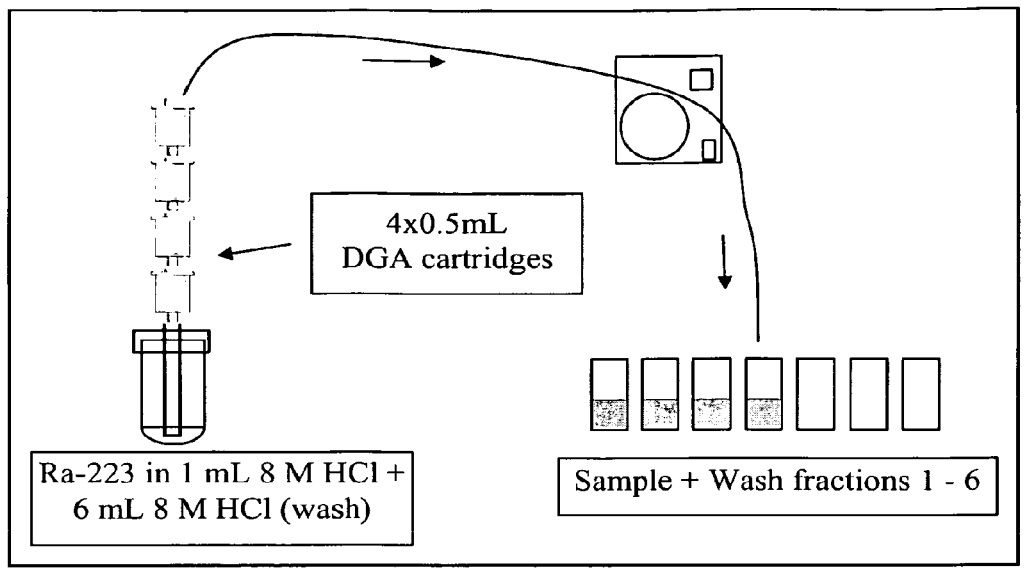
Figure 4 Experimental setup for DGA resin experiment 2
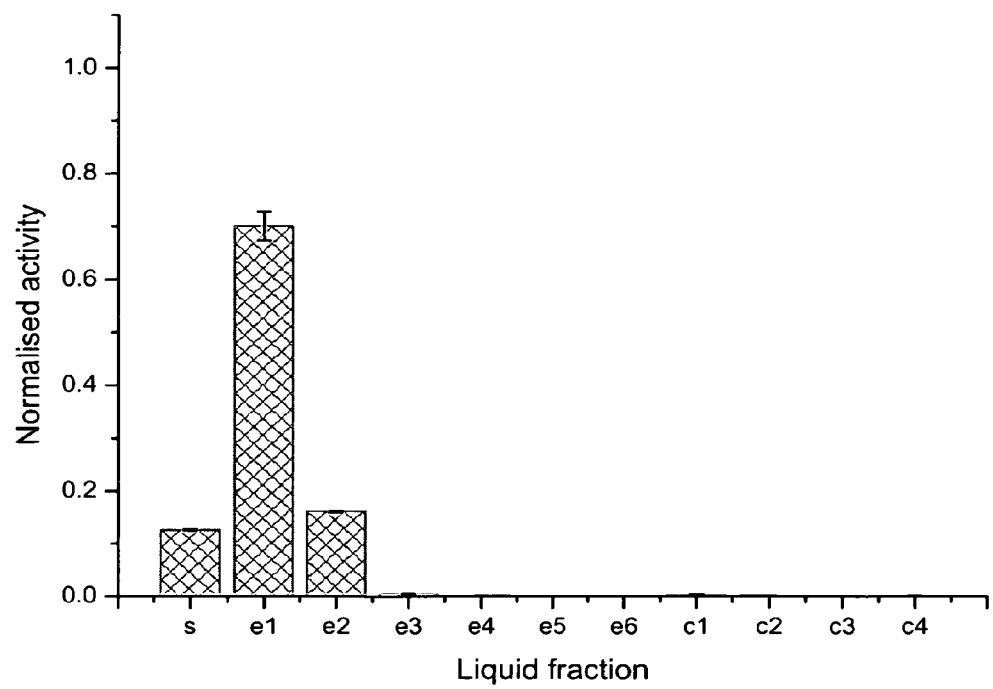
Figure 5 Normalised activity of $^{223}$Ra in various fractions (7×1 ml) and in the DGA-branched resin after elution. Error bars show 3 s.d. counting uncertainty.

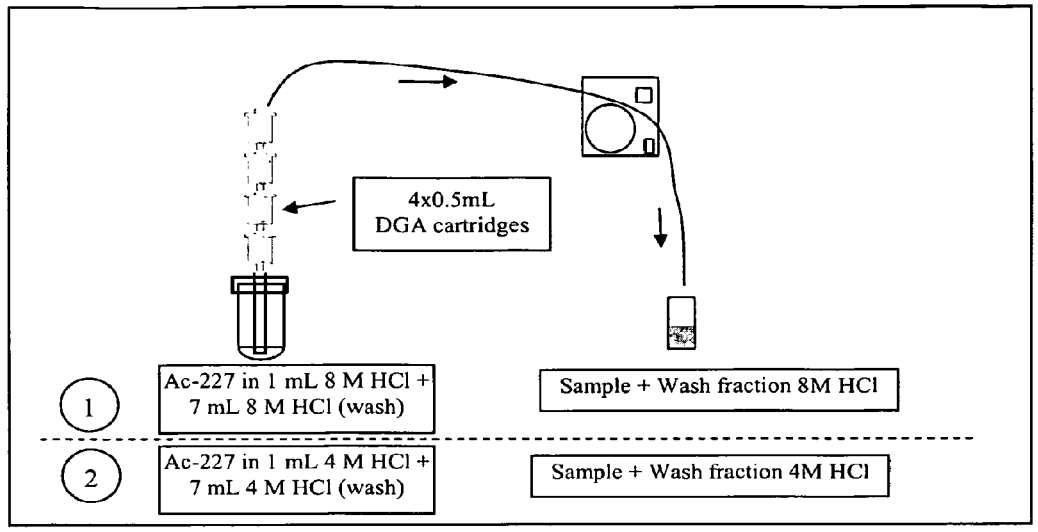
Figure 6 Experimental setup for DGA resin experiment 3
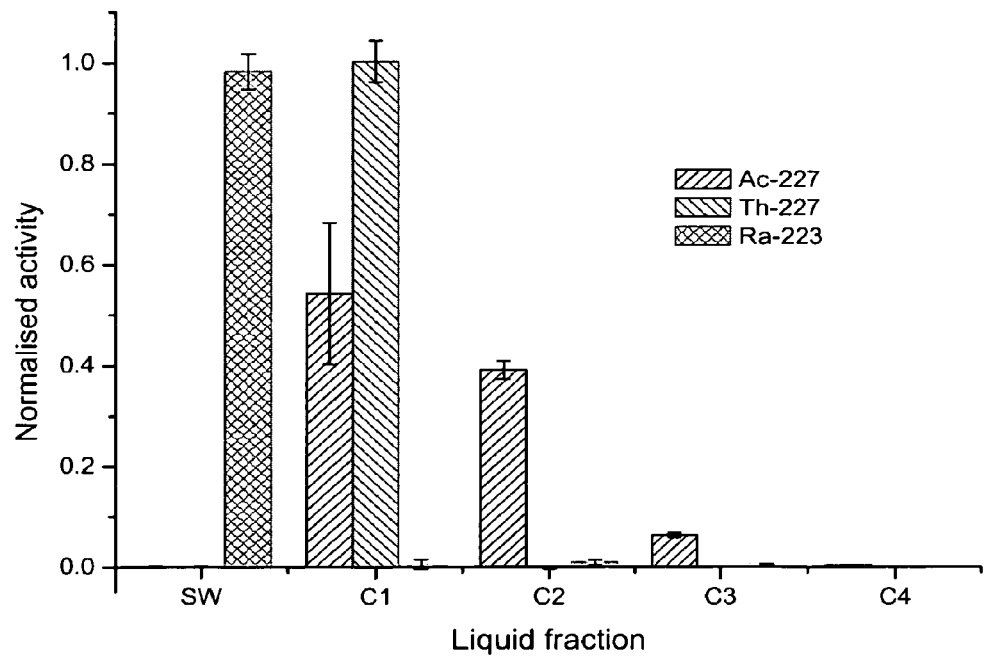
Figure 7 Normalised activity of $^{227}$Ac, $^{227}$Th and $^{223}$Ra in various fractions in the DGA-branched resin after elution. Error bars show 3 s.d. counting uncertainty. Legend: SW: sample + wash fraction (8 M HCl), C1-C4: cartridges after elution.

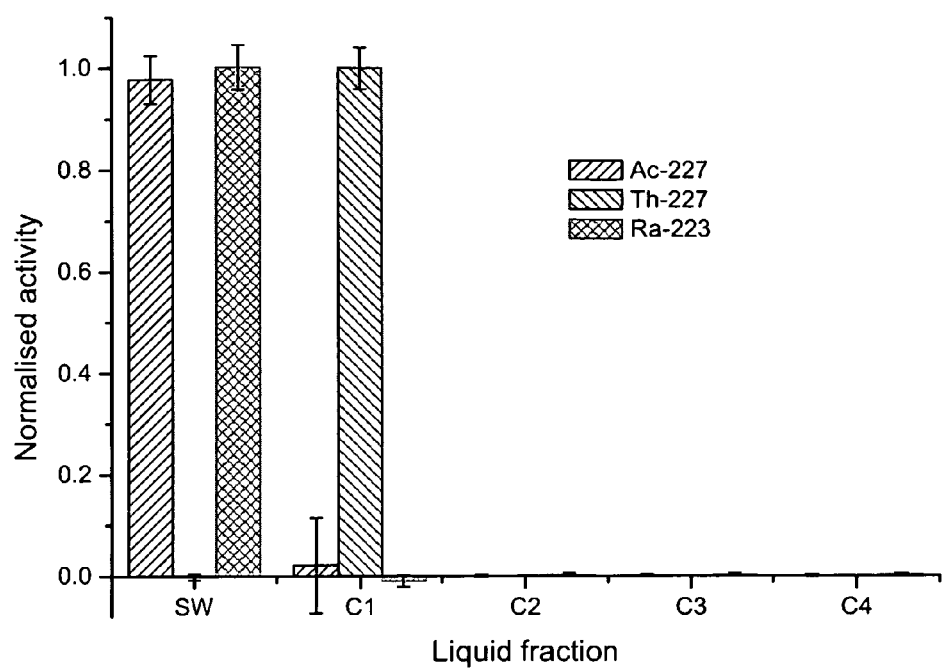
Figure 8 Normalised activity of $^{227}$Ac, $^{227}$Th and $^{223}$Ra in various fractions in the DGA-branched resin after elution. Error bars show 3 s.d. counting uncertainty.
Legend: SW: sample + wash fraction (4 M HCl), C1-C4: cartridge after elution.

ISOTOPE PRODUCTION METHOD

CROSS-REFERENCE TO RELATED APPLICATIONS

This application is the U.S. National Stage filing under 35 U.S.C. §371 of International Application No. PCT/EP2011/002156, filed Apr. 29, 2011, which claims the benefit of priority to Great Britain Patent Application No. 1007353.4, filed on Apr. 30, 2010.

FIELD OF THE INVENTION

The present invention relates to the preparation of radium-223 ($^{223}$Ra) for pharmaceutical use. In particular, the present invention relates to methods of the commercial-scale production of radium-223 having a purity acceptable for pharmaceutical administration to human subjects.

BACKGROUND TO THE INVENTION

Specific cell killing can be essential for the successful treatment of a variety of diseases in mammalian subjects. Typical examples of this are in the treatment of malignant diseases such as sarcomas and carcinomas. However the selective elimination of certain cell types can also play a key role in the treatment of many other diseases, especially immunological, hyperplastic and/or other neoplastic diseases.

The most common methods of selective treatment are currently surgery, chemotherapy and external beam irradiation. Targeted endo-radionuclide therapy is, however, a promising and developing area with the potential to deliver highly cytotoxic radiation to unwanted cell types. The most common forms of radiopharmaceutical currently authorised for use in humans employ beta-emitting and/or gamma-emitting radionuclides. There has, however, been a recent surge in interest in the use of alpha-emitting radionuclides in therapy because of their potential for more specific cell killing. One alpha-emitting nuclide in particular, radium-223 ($^{223}$Ra) has proven remarkably effective, particularly for the treatment of diseases associated with the bone and bone-surface.

The radiation range of typical alpha emitters in physiological surroundings is generally less than 100 micrometers, the equivalent of only a few cell diameters. This makes these nuclei well suited for the treatment of tumours, including micrometastases, because little of the radiated energy will pass beyond the target cells and thus damage to surrounding healthy tissue might be minimised (see Feinendegen et al., Radiat Res 148:195-201 (1997)). In contrast, a beta particle has a range of 1 mm or more in water (see Wilbur, Antibody Immunocon Radiopharm 4: 85-96 (1991)).

The energy of alpha-particle radiation is high compared to beta particles, gamma rays and X-rays, typically being 5-8 MeV, or 5 to 10 times that of a beta particle and 20 or more times the energy of a gamma ray. Thus, this deposition of a large amount of energy over a very short distance gives α-radiation an exceptionally high linear energy transfer (LET), high relative biological efficacy (RBE) and low oxygen enhancement ratio (OER) compared to gamma and beta radiation (see Hall, "Radiobiology for the radiologist", Fifth edition, Lippincott Williams & Wilkins, Philadelphia Pa., USA, 2000). This explains the exceptional cytotoxicity of alpha emitting radionuclides and also imposes stringent demands on the level of purity required where an isotope is to be administered internally. This is especially the case where any contaminants may also be alpha-emitters, and most particularly where long half-life alpha emitters may be present, since these can potentially cause significant damage over an extended period of time.

One radioactive decay chain leading to $^{223}$Ra, which has been used as a source for this isotope in small quantities, is indicated below. The table shows the element, molecular weight (Mw), decay mode (mode) and Half-life (in years (y) or days (d)) for $^{223}$Ra and its two precursor isotopes. This preparation begins from $^{227}$Ac, which is itself found only in traces in uranium ores, being part of the natural decay chain originating at $^{235}$U. One ton of uranium ore contains about a tenth of a gram of actinium and thus although $^{227}$Ac is found naturally, it is more commonly made by the neutron irradiation of $^{226}$Ra in a nuclear reactor.

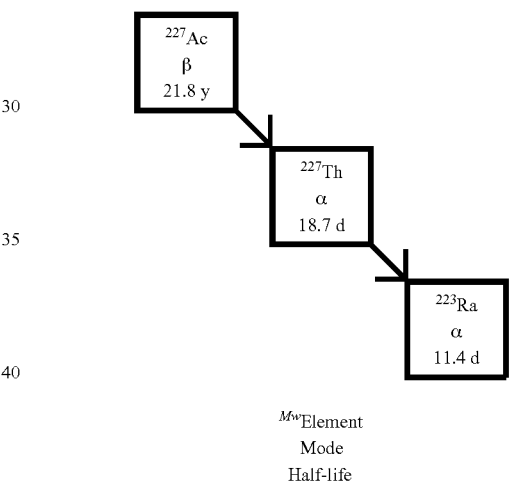

$^{Mw}$Element
Mode
Half-life

It can be seen from this illustration that $^{227}$Ac, with a half-life of over 20 years, is a very dangerous potential contaminant with regard to preparing $^{223}$Ra from the above decay chain for pharmaceutical use. In particular, although $^{227}$Ac itself is a beta-emitter, its long half-life means that even very low activities represent a significant lifetime radiation exposure, and furthermore, once it decays, the resulting daughter nuclei generate a further 5 alpha-decays and 2 beta-decays before reaching stable $^{207}$Pb. These are illustrated in the table below:

| Nuclide | $^{227}$Th | $^{223}$Ra | $^{219}$Rn | $^{215}$Po | $^{211}$Pb | $^{211}$Bi | $^{207}$Tl | $^{207}$Pb |
|---|---|---|---|---|---|---|---|---|
| ½-life | 18.7 d | 11.4 d | 4.0 s | 1.8 ms | 36.1 m | 2.2 m | 4.8 m | stable |
| α-energy/MeV | 6.15 | 5.64 | 6.75 | 7.39 | | 6.55 | | |
| β-energy (max)/MeV | | | | | 1.37 | | 1.42 | |
| Energy % | 17.5 | 16.0 | 19.1 | 21.0 | 3.9 | 18.6 | 4.0 | |

It is evident from the above two decay tables that more than 35 MeV of energy is deposited by one $^{227}$Ac decay chain, representing a significant toxicity risk for essentially the entire lifetime of any human subject administered with $^{227}$Ac.

Based on radium-223 production from a $^{227}$Ac source, actinium-227 (half-life=21.8 years) is the only likely radionuclide contaminant with a long half-life. Limits for allowed intake of different radionuclides by healthy workers are proposed by the International Commission of Radiological Protection (ICRP) and maximum allowable exposure can be calculated based upon this recommendation and proposed therapeutic doses. The upper limit for actinium-227 is suggested to be 50% of the most restrictive ALI value for oral intake of actinium-227. This gives 0.0045% activity based on a total dose of 300 kBq/kg b.w. (for example 50 kBq/kg b.w.×6 injections) and a patient weight of 80 kg.

In view of the above, the content of $^{227}$Ac contaminant in $^{223}$Ra for pharmaceutical use should be strictly limited to 45 Bq $^{227}$Ac in 1 MBq $^{223}$Ra. Thus for practical purposes, a method which is to provide $^{223}$Ra for pharmaceutical use should preferably provide a purity of 10 Bq $^{227}$Ac in 1 MBq $^{223}$Ra or better to ensure that this safety limit is always adhered to.

A number of studies into the purification of $^{223}$Ra have been published, primarily in environmental contexts, where the authors desire to accumulate the $^{223}$Ra from a high-volume sample so as to allow analysis of the degree of environmental contamination.

Only one previously published method is known to have directly addressed the question of generating $^{223}$Ra with biomedical purity, and that is the method of Larsen et al. published in WO/2000/040275. In this method, the involved to permanent absorption of $^{227}$Ac and $^{227}$Th onto an f-block specific Silica Actinide Resin having P,P' di-octyl methane bisphosphonic acid binding groups on a silica support. This provided relatively high purity, of less than $4\times10^{-3}$% $^{227}$Ac in comparison with $^{223}$Ra, but required a large number of manual handling steps and was poorly suited for scaling-up or automation. Furthermore, because the resin irreversibly absorbed the mother and grandmother nuclei, the issue of radioactive damage to the resin becomes significant if such a resin is to be used for the commercial lifetime of an $^{227}$Ac source (tens of years). This is especially the case on a commercial scale, where concentrations of isotopes need to be kept as high as possible to maximise batch sizes and minimise handling volumes.

No previously known method for the generation of $^{223}$Ra addresses issues such as yield of $^{223}$Ra, speed of the purification process, automation, minimising of wasted isotopes and corresponding production or radioactive waste or any similar issues associated with commercial-scale production. Furthermore, all methods known to produce $^{223}$Ra of viable pharmaceutical purity use specialist resins which cannot be guaranteed to be available and are potentially more difficult to validate as reliable. Guseva et al. (Radiochemistry 46, 58-62 (2004)) proposed a basic generator system for $^{223}$Ra using an anion exchange method developed for extracting radium from environmental samples. This, however, was on a very small scale and never intended or indicated as providing material of pharmaceutical purity.

One other method for selective binding of f-block elements which has been applied to the purification of lanthanides/actinides from radium is that of Horwitz in U.S. Pat. No. 7,553,461. U.S. Pat. No. 7,553,461 describes a diglycomide (DGA) extractant which can be attached to a resin and used to separate f-block elements from those of the main group. Unlike the actinide resin previously discussed, this extractant allows for the regeneration of an f-block generator mixture after separation and thus does not require that the resin be stable in perpetuity. Because the f-block elements can be released, Horwitz describes this as a method for removing cations such as radium from f-block elements where the radium is considered a contaminant. The radium is washed through a column of DGA resin and disposed of leaving the purified and decontaminated actinide element to be stripped from the column.

The DGA resin described in Horwitz is only demonstrated to provide a separation efficiency of $10^2$ for $^{223}$Ra over $^{227}$Ac (U.S. Pat. No. 7,553,461, column 19 line 9). This is in the context of removing the radium and this it is not clear how applicable this would be to the preparation of radium rather than actinium, but even if this separation efficiency applied, it would fall well short of the at least $10^4$ separation efficiency required to prepare pharmaceutical standard $^{223}$Ra from a $^{227}$Ac generator mixture. Thus, if the resin described in U.S. Pat. No. 7,553,461 were used then this would apparently require two consecutive columns.

In view of the above, there is a considerable need for an improved method by which $^{223}$Ra may be generated and purified for pharmaceutical use at a purity appropriate for direct injection into human subjects. It would be a considerable advantage if the method were to provide a high yield of $^{223}$Ra, a low loss of $^{227}$Ac or $^{227}$Th parent isotopes and/or utilise only a small number of separation steps. It would be further advantageous if the method was rapid, was viable for relatively large (commercial scale) radioactive samples, included only a minimum number of manual handling steps, and/or was suitable for automation.

BRIEF DESCRIPTION OF THE INVENTION

The present inventors have now established that by optimising the conditions of use, and particularly by employing a combination of both forward and reverse flow, a highly effective separation of $^{223}$Ra from an $^{227}$Ac/$^{227}$Th generator mixture can be provided using only a single diglycolamide (DGA) extraction step. Furthermore, the generator mixture can be regenerated with an efficiency not previously reported. Recovery of both the $^{227}$Th and $^{227}$Ac allows for the potential long term, rapid-turnover, use of the system.

In a first aspect, the present invention therefore provides a method for the generation of $^{223}$Ra of pharmaceutically tolerable purity comprising i) preparing a generator mixture comprising $^{227}$Ac, $^{227}$Th and $^{223}$Ra in a first aqueous solution comprising a first mineral acid;

ii) loading said generator mixture onto a DGA separation medium (e.g. resin);

iii) eluting said $^{223}$Ra from said DGA separation medium using a second mineral acid in a second aqueous solution to give an eluted $^{223}$Ra solution; and iv) stripping the DGA separation medium of said $^{227}$Ac and $^{227}$Th by flowing a third mineral acid in a third aqueous solution through the DGA separation medium in a reversed direction (i.e. reverse flow);

The process will optionally and preferably also include the step of:

y) storing said mixture of $^{227}$Ac and $^{227}$Th for a period sufficient to allow ingrowth of $^{223}$Ra by radioactive decay, whereby to re-form a generator mixture comprising $^{227}$Ac, $^{227}$Th and $^{223}$Ra.

Further manipulation and/or preparation steps may be carried out on the eluted $^{223}$Ra solution subsequent to step iii), however, the $^{223}$Ra present in the eluted $^{223}$Ra solution will preferably be of sufficient radiochemical purity for pharmaceutical use without further separation. Thus, in a preferred aspect of the invention, $^{223}$Ra of pharmaceutical purity is generated from a generator mixture comprising $^{227}$Ac, $^{227}$Th and $^{223}$Ra in a single separation step. This is preferably possible on a commercial scale and using a method suitable for long-term application.

After ingrowth step y), the generator mixture may be re-used to generate a further batch of $^{223}$Ra, and a single $^{227}$Ac sample will preferably be used repeatedly (e.g. more than 10 times, such as 50 to 500 times). It is therefore preferable that the process be repeated from step i), or step ii) as appropriate.

In a further aspect, the present invention provides a solution or preparation of $^{223}$Ra comprising less than 45 Bq $^{227}$Ac per 1 MBq $^{223}$Ra. Such a solution or preparation is optionally formed or formable by any of the methods herein described, and is preferably formed or formable by the preferred methods herein described. Such solutions and/or preparations may be comprised in a pharmaceutical composition, such as one also comprising at least one pharmaceutically tolerable carrier and/or diluent.

DETAILED DESCRIPTION OF THE INVENTION

A very significant aspect of the present invention is the ability for the generator mixture to be stripped from the separation medium (e.g. resin) and regenerated with high efficiency. In particular, the present method relates to a process for long-term commercial use, and as such should be capable of allowing the repeated use of the generator mixture for many years. The useful life of the generator mixture will certainly be of the order of the half-life of the originating $^{227}$Ac isotope, and thus potentially several tens of years (e.g. 10 to 50 years). There are several issues which result from this which have not been addressed in any of the $^{223}$Ra production or purification systems previously described.

A first issue arising from the potentially long commercial lifetime of the generator mixture is the stability of its storage environment. Specifically, any material exposed to the a relatively small 10 GBq generator mixture is potentially receiving more than a million beta decays per second from the $^{227}$Ac, plus around the same number of alpha decays per second from the included $^{227}$Th and up to the same number of alpha decays again from the in-growing $^{223}$Ra and from each of the other daughter products further down the decay chain.

Alpha irradiation in particular is highly ionising and so over the course of a number of years, the $10^{13}$ or more alpha-decays per year to which the surroundings of a modest 10 GBq generator will be exposed is very likely to cause significant damage to any organic components in long term proximity. As a result, systems such as those described in WO/2000/040275, in which the generator is irreversibly bound to a separator resin cannot be expected to be stable even when inorganic resins are used, since the binding components closest to the radionuclei are organic and susceptible to damage. This will result in gradual loss of binding capacity and eventual loss of generator material and radiochemical purity of the $^{223}$Ra.

In view of the likely damage by long-term exposure, it would be a considerable advantage if the generator mixture could be regenerated from the separation system so that new separation material could be used periodically. This not only avoids loss of the generator mixture but also guarantees that the purity of the product will be as high after several decades as it was when the system was first employed. In the present method, the generator system will thus be regenerated from the separation material after every use.

In a corresponding aspect, the present invention additionally provides for a method for the generation of $^{223}$Ra of pharmaceutically tolerable purity wherein the parent isotope(s) (i.e. the generator system) are stored as a salt (e.g. in solid form or in solution) and contacted with a separation medium only when separation of $^{223}$Ra is required (e.g. for no more than 1 day every 1-8 weeks, preferably no more than 1 day every 2 to 6 weeks.

Where a generator mixture is regenerated from a separation medium it is important that this happen to a very high degree. As noted above, the actinide specific resin described for use in WO/2000/040275 does not allow for regeneration of the generator mixture, since this is bound irreversibly. This is acceptable for laboratory or short-term testing use but is a potential problem for long-term use at a commercial scale as described above. Although DGA resin is known to be compatible with elution of $^{227}$Ac, the behaviour of this separation medium with thorium ions has not previously been investigated.

The present applicants have, by optimisation of conditions established that the regeneration capacity of the described DGA system can provide recover of 99.9% of the loaded $^{223}$Ac on a viable commercial scale. This amounts to a loss of only 0.1% of the $^{227}$Ac generator per cycle.

Great difficulty has, however, been met in attempting to generate the $^{227}$Th intermediate isotope since this could not be significantly eluted using any method known prior to the present invention.

Assuming that the generator is used every 3 week (after 72% of the possible maximum ingrowth of $^{223}$Ra), then regeneration occurs 17 times a year. The loss of only 0.1% of the generator isotope would thus result in a reduction in activity of around 1.7% in a year. Due to the 21 year half-life of the isotope, however, the natural reduction in activity would be around 3.2% per year in any case and so this loss is an acceptable one.

A complete inability to recover any part of the $^{227}$Th (as was effectively the case prior to the present invention) would, however, present a potentially much more significant issue in a commercial context. In particular, a theoretical 1 GBq generator system beginning with 1 GBq of $^{227}$Ac and 1 GBq of $^{227}$Th will generate 726 MBq $^{223}$Ra in 21 days. In the absence of any $^{227}$Th recovery, however, this reduces to only 265 MBq in 21 days (less than 37%). In practice, this would mean that the generator mixture could not be effectively re-used until sufficient in-growth of $^{227}$Th had occurred, thereby increasing the generator cycle time and reducing both the number of cycles per year and the total lifetime yield of the generator system.

Assuming no recovery of the $^{227}$Th then a 1 Gb $^{227}$Ac generator would take around 55 days to form 722 MBq of $^{223}$Ra (equivalent to 21 days on a fully recovered system). This then reduces the number of cycles per year from 17 to less than 7, and the total yearly yield of pure $^{223}$Ra from 12 GBq to only 5 GBq $^{223}$Ra. The present inventors have, however, established that by use of a suitable low-concentration mineral acid solution and reverse-flow conditions, 95-99.5% of the $^{227}$Th from the generator mixture can be recovered. This means that the generator will be ready for separation of the $^{223}$Ra within only 21 days and allows the full 17 cycles per year. This increases the useful yield of the column by a factor of 2.4 and reduces $^{227}$Th the radioactive waste by the same proportion.

There is no known method which has previously allowed the separation of pharmaceutical purity $^{223}$Ra in a single step followed by recovery of more than 99% of the $^{227}$Ac and up to 99% (e.g. 80 to 99%) of the $^{227}$Th generator isotopes. As discussed above, this doubles the potential production of the generator and correspondingly reduces the generated radioactive waste very considerably.

The method of the present invention, as well as all other aspects, relates to the use of a diglycolmide (DGA) separation medium. Such a medium is described in U.S. Pat. No. 7,553,461 (incorporated by reference) and may comprise a diglycolmide moiety optionally attached, bonded or sorbed to a support. A preferred DGA separation medium is a DGA resin and such a resin may be used in any compatible embodiment of the invention. Thus, while DGA resin is used as an example DGA separation medium herein, other DGA separation media may be used in all compatible embodiments, but DGA resin is typically preferred.

The "DGA" groups as referred to herein may be any suitable diglycolamide, such as those of formula DGA1 below:

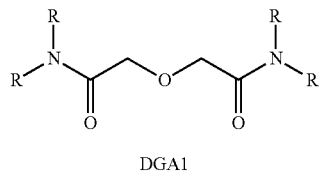

DGA1

Wherein each R group is independently hydrogen or a hydrocarbyl group, where the four R groups collectively contain around 10 to 60 carbon atoms, more typically around 15 to 40 carbon atoms. Preferably each R group will be a hydrocarbyl group, and in one embodiment, all R groups are the same hydrocarbyl group, such that they collectively have 16, 20, 24, 28, 32, 36 or 40 carbon atoms in highly preferred embodiments. Preferred hydrocarbyl groups include C8 alkyl groups such as n-octyl and 2-ethylhexyl. A most preferred R group is 2-ethylhexyl, such that a highly preferred DGA moiety is N,N,N',N'-tetra-2-ethylhexyldiglycolamide (formula DGA1 where each R group is 2-ethylhexyl). This may be attached at any suitable position to any suitable resin (such as those described herein and in U.S. Pat. No. 7,553,461) directly or by means of a linker moiety such as a hydrocarbyl linker.

With regard to optional but highly preferable step y), the regeneration of the $^{223}$Ra will begin by natural radioactive decay as soon as the existing $^{223}$Ra is eluted in step iii). It is preferable to allow sufficient time for significant ingrowth of $^{223}$Ra before the generator mixture is again separated, and the period which is suitable will depend upon the nature of the mixture, as discussed above. Preferably, the recovery of the mixture will be sufficiently effective (as described herein) that the $^{227}$Th activity will be close to 99% of the $^{227}$Ac activity. In such circumstances a period of around 14 to 60 days is suitable for allowing ingrowth of $^{223}$Ra. This would provide between around 520 MBq and 975 MBq $^{223}$Ra from a theoretical mixture of 1 GBq $^{227}$Ac and 1 GBq $^{227}$Th. Where the $^{227}$Th level is significantly depleted by reduced recovery, this period will be longer, particularly towards the shorter end of the range. The skilled worker will have no difficulty selecting a suitable ingrowth period based upon the characteristics of each particular system.

The present invention provides a method for the production of $^{223}$Ra at a purity suitable for use in endo-radionuclide therapy. A number of preferred features of the system are indicated below, each of which may be used in combination with any other feature where technically viable, unless indicated otherwise.

Step i) of the method of the invention relates to preparing a generator mixture comprising $^{227}$Ac, $^{227}$Th and $^{223}$Ra in a first aqueous solution comprising a first mineral acid. Such a mixture will inherently form by the gradual decay of a sample of $^{227}$Ac, but for use in the invention will preferably also have one or more of the following features, either individually or in any viable combination:
a) an $^{227}$Ac radioactivity of at least 500 MBq (e.g. 500 MBq to 50 GBq), preferably at least 1 GBq, more preferably at least 2.5 GBq (e.g. 1 to 10 GBq);
b) a $^{223}$Ra radioactivity of at least 100 MBq (e.g. 100 MBq to 50 GBq), preferably at least 350 MBq, more preferably at least 1 GBq;
c) a volume of no more than 10 column volumes (e.g. 0.1 to 10 column volumes), no more than 5 column volumes ml, more preferably in the range 0.1-1.5 column volumes.
d) The first mineral acid may be an acid selected from $H_2SO_4$, $HNO_3$ and HCl, preferably HCl
e) The concentration of the first mineral acid may be at least 3 M, (e.g. 3 to 12M), preferably at least 4M, more preferably more than 6M, most preferably around 8M.

Step ii) of the method of the invention relates to loading the generator mixture onto a DGA separation medium (e.g. DGA resin) which will typically comprise a DGA moiety and a support, such as an organic or inorganic support (e.g. resin). This step and the entities referred to therein may have the following preferable features, either individually or in any viable combination, and optionally in any viable combination with any of the features of the other steps as described herein:
a) The DGA moiety may have $R_1R_2NCO_2CH_2OCH_2CO_2NR_3R_4$ binding groups wherein $R_1$, $R_2$, $R_3$, and $R_4$ are the same or different hydrocarbyl groups having collectively 14 to 60 carbon atoms, such as those described in U.S. Pat. No. 7,553,461;
b) The DGA moiety may be supported on an inorganic or organic support, such as porous silica or polystyrene particles.
c) The DGA moiety may have N,N,N',N' tetra-alkyl (e.g. n-octyl or 2-ethylhexyl)diglycolamide binding groups;
d) The DGA moiety may be sorbed onto particles having a size of 10 to 400 μM, preferably 20 to 200 μm, more preferably 50 to 100 μm.
e) The DGA moiety may be a resin and may be used in the form of a column.
f) The volume of resin used (e.g. when packed in a column) may be 10 ml or less, (e.g. 0.5 to 10 ml), preferably 5 ml or less, more preferably 1 to 2.5 ml (e.g. around 2 ml).
g) The DGA resin may be Eichrom DGA Resin or equivalent resin with a 50-100 μm particle size.

Step iii) of the method of the invention relates eluting the $^{223}$Ra from the DGA separation medium using a second mineral acid in a second aqueous solution to give an eluted $^{223}$Ra solution. This step and the entities referred to therein may have the following preferable features, either individually or in any viable combination, and optionally in any viable combination with any of the features of the other steps as described herein:
a) The second mineral acid may be an acid selected from $H_2SO_4$, $HNO_3$ and HCl, preferably HCl. This may be the same as or different from the first mineral acid but will preferably be the same.
b) The second mineral acid may be used at a concentration of at least 3 M, (e.g. 3 to 12M), preferably at least 4M, more preferably more than 6M, most preferably around 8M. The concentration may be the same as or different to that of the first mineral acid but will preferably be the same.
c) The $^{223}$Ra may be eluted from said DGA separation medium using 0.1 to 10 column volumes of the second mineral acid in aqueous solution. Preferably the amount will be 0.5 to 5 column volumes, more preferably 1 to 3 column volumes (e.g. around 1-2 column volumes).
d) The first eluted solution will preferably have a contamination level of no more than 45 (e.g. 0.1 to 45) Bq $^{227}$Ac per 1 MBq $^{223}$Ra, more preferably no more than 15 Bq $^{227}$Ac per 1 MBq $^{223}$Ra and most preferably no more than 3 Bq $^{227}$Ac per 1 MBq $^{223}$Ra;
e) The steps of loading the generator mixture onto the DGA separation medium and eluting the first eluted $^{223}$Ra solution may provide a separation ratio of $^{223}$Ra to $^{227}$Ac of at least 10,000:1 (e.g. 10,000:1 to 500,000:1), preferably at least 50,000:1, more preferably at least 100,000:1.
f) The yield of $^{223}$Ra eluted from the DGA separation medium will preferably be no less than 60% relative to the amount loaded onto the DGA separation medium in step ii). This will preferably be no less than 75%, more preferably no less than 80%. A $^{223}$Ra yield of around 90% or more is more preferred.
g) The $^{223}$Ra may be eluted from said DGA separation medium in uncomplexed form, such as in the form of a simple salt in solution (e.g. as the salt of the second mineral acid).
h) The use of complexing agents such as DTPA may be avoided, and in one embodiment all solutions used in step ii and/or step iii are substantially free of complexing agents, such as DTPA.

Step iv) of the method of the invention relates to stripping the DGA separation medium of the $^{227}$Ac and $^{227}$Th by flowing a third mineral acid in a third aqueous solution through the DGA separation medium (e.g. resin) in a reversed direction. This step and the entities referred to therein may have the following preferable features, either individually or in any viable combination, and optionally in any viable combination with any of the features of the other steps as described herein:
a) The third mineral acid may be an acid selected from $H_2SO_4$, $HNO_3$ and HCl, preferably HCl. This may be the same as or different from the first and/or the second mineral acid but will preferably be the same as both.
b) The third mineral acid may be used at a concentration lower than that of the first and/or second mineral acids. Preferably lower by a factor of at least 10, more preferably lower by a factor of at least 50.
c) The third mineral acid may be used at a concentration of 0.01 to 3M, preferably 0.05 to 0.2 M, more preferably around 0.1M;
d) The $^{227}$Ac and $^{227}$Th may be stripped from the DGA separation medium using 1 to 30 column volumes of the third mineral acid in aqueous solution. Preferably the amount will be 3 to 20 column volumes, more preferably 5 to 10 column volumes.
e) The flow of the third mineral acid in aqueous solution is indicated herein to be "in a reversed direction". This is used to indicate a direction of flow opposite to that used in steps ii) and iii) when loading the generator mixture and eluting the desired $^{223}$Ra. The direction of loading of the generator mixture is thus considered the "forward" direction, and all flow is intended to be in that direction unless indicated to be in the reversed direction or to be reversed flow. Where the flow is in the reversed direction, flow rate may be 0.02-1 cv/min (Column volume pr min)
f) The stripping of said $^{227}$Ac and $^{227}$Th from the DGA separation medium may regenerate greater than 99% e.g. 99 to 99.9%) of the $^{227}$Ac loaded onto the resin in step ii). Preferably this will be greater than 99.5%. Around 99.9% is most preferred.
e) The elution of said $^{227}$Ac and $^{227}$Th from said DGA separation medium may regenerate greater than 70% (e.g. 70 to 99.5%) of the $^{227}$Th loaded onto the resin in step ii). Preferably this will be greater than 85%, and more preferably at least 90%. Around 95-99% or more is most preferred.
g) The $^{227}$Ac and $^{227}$Th may be eluted from said DGA separation medium in uncomplexed form, such as in the form of a simple salt in solution (e.g. as the salt of the third mineral acid).
h) The use of complexing agents such as DTPA may be avoided, and in one embodiment all solutions used in step iv are substantially free of complexing agents, such as DTPA.

A further factor which is of considerable significance to a commercial process is speed. With all handling relating to radioisotopes, the material will be continuing to decay at all times. This is particularly an issue with a pharmaceutical product for large-scale production, since this must be prepared, analysed, assayed and validated, distributed and administered before the dose changes significantly. With a $^{223}$Ra product having an 11-day half-life, this puts considerable pressure on every step of the process. It is preferable, therefore, that the number of steps in the procedure should be as few as possible, and furthermore that the process be as rapid as possible without compromising radiochemical purity. Faster manipulation also allows for larger doses and higher concentrations to be handled because the radiolysis of the separation media may be a limiting factor. The exposure of the separation media is the product of the activity and the contact time, and thus by reducing contact time a greater activity may be handled without risk of losing separation efficiency.

Due to the highly optimised conditions developed by the present inventors, it is possible to handle relatively large batches e.g. 1 to 50 GBq) of generator mixture on a low volume of separation resin, eluting with the minimum volume of solvent compatible with a high level of purification. As a result, the period between the start of loading step ii) and elution of the purified $^{223}$Ra in step iii) can be brought down to no more than 4 hours (e.g. 0.5 to 4 hours). This will preferably be no more than 2.5 hours, preferably no more than 1 hours. The recovery step may be carried out over any desired period, but will also preferably be accomplished in less than 1 hour.

The invention will now be illustrated further by reference to the following non-limiting examples and the attached figures, in which:

FIG. 1 Shows the natural in growth of various daughter isotopes into a sample of $^{227}$Ac;

FIG. 2 Shows a schematic representation of the experimental setup for the reversed flow method of DGA resin experiment 1

FIG. 3 Shows the recovery of isotopes by the method of DGA resin experiment 1

FIG. 4 Shows a schematic representation of the experimental setup for the method of DGA resin experiment 2;

FIG. 5 Shows the elution of $^{223}$Ra in various fractions in the method of DGA resin experiment 2;

FIG. 6 Shows a schematic representation of the experimental setup for the method of DGA resin experiment 3;

FIG. 7 Shows the distribution of $^{227}$Ac in the fractions collected by the method of DGA resin experiment 3;

FIG. 8 Shows the distribution of isotopes in the fractions collected by the method of DGA resin experiment 3 when an alternative solution is used;

EXAMPLES

DGA Branched

The DGA resin has attractive properties for use in the $^{223}$Ra separation process as it has the capability of separating Ra from Ac, and to recover Ac. It is highly desirable to also recover $^{227}$Th as it significantly decreases the ingrowth time of $^{223}$Ra. FIG. 1 shows that about 8 weeks is needed to have 72% ingrowth of $^{223}$Ra in $^{227}$Ac, if $^{227}$Th is not present. However if $^{227}$Th is recovered, about 60% less $^{227}$Ac and thus correspondingly less time is required to produce the same $^{223}$Ra amount.

Previous experiments showed that $^{227}$Th was difficult to recover from the resin in a sufficiently small volume using normal flow conditions.

DGA Resin Experiment 1

In this experiment, reverse flow was used on the strip solution. The experimental details for the experiment are summarised in Table 1.

TABLE 1

Experimental protocol for DGA-branched resin - factory pre-packed in 2 ml Supelco cartridge.

| Sample ID | Solutions | Volume | Description |
|---|---|---|---|
| Eq 1 | 8M HCl | 12 ml | Equilibration |
| S | $^{227}$Ac in 8M HCl | 1 ml | Sample |
| W | 8M HCl | 2 ml | Wash |
| E1 | 0.1M HCl | 3 ml | Strip |
| E2 | 0.1M HCl | 3 ml | Strip |
| E3 | 0.1M HCl | 3 ml | Strip |
| E4 | 0.1M HCl | 3 ml | Strip |
| E5 | 0.1M HCl | 3 ml | Strip |
| E6 | 0.1M HCl | 3 ml | Strip |
| E7 | 0.1M HCl | 3 ml | Strip |
| C | n.a. | Resin | Cartridge |

The normalised activity of $^{227}$Ac, $^{227}$Th and $^{223}$Ra in various liquid fractions and in the cartridge are shown in FIG. 3. The results show excellent separation of $^{223}$Ra from its predecessors in the load fraction (S and W). The calculations based on $^{227}$Th measurements show that the $^{227}$Ac activity in the SW fractions are −1.4±1.87 Bq, i.e. between 0 and 0.47 Bq based on 3 s.d. counting uncertainty. This can be compared to the $^{227}$Ac activity before separation of $2.4 \times 10^5 \pm 9 \times 10^3$ Bq. Thus by using the highly conservative 0.47 Bq, the $^{227}$Ac separation efficiency is approximately 500000. The $^{227}$Ac/$^{223}$Ra ratio in the SW fraction therefore becomes between 0 and 2.3 Bq$_{Ac}$/MBq$_{Ra}$ based on 3 s.d. counting uncertainty. This number can be compared with the current limit of 45 Bq$_{Ac}$/MBq$_{Ra}$ in the Alpharadin drug product specification, i.e. the DGA resin is able to separate $^{223}$Ra from $^{227}$Ac to levels well below the specified limit.

Furthermore, the results presented in FIG. 3 show a recovery of all detectable $^{227}$Ac and most $^{227}$Th in the first 6 ml of strip solution (E1-E2) when using reverse flow operation. In the E3-E7 fractions and cartridge no significant $^{227}$Ac activity and approximately 3% of $^{227}$Th could be detected. The yield loss of $^{223}$Ra through the cartridge is also insignificant.

At first glance it might seem peculiar that the fractions with the highest activity also are associated with relatively high uncertainties. The reason is that $^{227}$Ac activities are indirectly estimated from the $^{227}$Th activity as described previously. The calculations are further complicated as ingrowth of $^{227}$Th and $^{223}$Ra from the indirectly determined $^{227}$Ac must be subtracted from the HPGe detector data so that the nuclide activities can be calculated back to the time for separation. Due to this some $^{227}$Th and $^{223}$Ra values will also become associated with relatively high uncertainties.

DGA Resin Experiment 2

The elution of $^{223}$Ra through the DGA branched resin was studied in a separate experiment to confirm the low yield loss of $^{223}$Ra from the previous experiment. By using a $^{223}$Ra solution without its parents, the uncertainty in the $^{223}$Ra data becomes unaffected by ingrowth from $^{227}$Ac. Experimental details are given in Table 2. The experimental setup is shown schematically in FIG. 4.

TABLE 2

Experimental protocol for DGA-branched resin - packed in four 0.5 ml Supelco cartridges.

| Sample ID | Solutions | Volume | Description |
|---|---|---|---|
| Eq1 | 8M HCl | 20 ml | Equilibration |
| S | $^{223}$Ra in 8M HCl | 1 ml | Sample |
| E1 | 8M HCl | 1 ml | Wash |
| E2 | 8M HCl | 1 ml | Wash |
| E3 | 8M HCl | 1 ml | Wash |
| E4 | 8M HCl | 1 ml | Wash |
| E5 | 8M HCl | 1 ml | Wash |
| E6 | 8M HCl | 1 ml | Wash |
| C1 | n.a. | resin | Cartridge |
| C2 | n.a. | resin | Cartridge |
| C3 | n.a. | resin | Cartridge |
| C4 | n.a. | resin | Cartridge |

The results presented in FIG. 5 confirm the previous results and show that approximately 99.5% of $^{223}$Ra passes through the 2 ml cartridge using 1 cartridge volume of wash (S, E1-E2), This has the advantages that a small volume of 1 ml load+2 ml wash is needed to separate $^{223}$Ra from its predecessors and that the contact time is minimised as the load and wash procedure takes approximately 3 minutes using a flow rate of 1 ml/min.

DGA Resin Experiment 3

The objective of this experiment was to investigate the performance of the DGA-branched resin when loading $^{227}$Ac at two different molar concentrations (8 M HCl and 4 M HCl) and using a wash volume of 7 ml (compared with the 2 ml needed for $^{223}$Ra separation found in DGA experiment 2). Experiments were conducted with four stacked 0.5 ml cartridges. The experimental protocols are shown in. The experimental setup is shown schematically in FIG. 6.

TABLE 3

Experimental protocol for DGA-branched resin - packed in four 0.5 ml Supelco cartridges.

| Sample ID | Solutions (8M HCl exp.) | Solutions (4M HCl exp.) | Volume | Description |
|---|---|---|---|---|
| Eq1 | 8M HCl | 4M HCl | 20 ml | Equilibration |
| S | $^{227}$Ac in 8M HCl | $^{227}$Ac in 4M HCl | 1 ml | Sample |
| W | 8M HCl | 4M HCl | 7 ml | Wash |
| C1 | n.a. | n.a. | resin | Cartridge |
| C2 | n.a. | n.a. | resin | Cartridge |
| C3 | n.a. | n.a. | resin | Cartridge |
| C4 | n.a. | n.a. | resin | Cartridge |

The results show that most of the $^{227}$Ac is distributed in the first and second cartridges after 7 ml 8 M HCl wash solution has been added (see FIG. 7)

No significant $^{227}$Ac was detected in the SW fraction, i.e. no leaching of $^{227}$Ac could be detected after washing with 3.5 times more 8 M HCl than needed for $^{223}$Ra separation. Th-227 is fully retained in the first quarter of the cartridge while $^{223}$Ra is fully recovered in the SW fraction.

When using 4 M HCl instead of 8 M HCl for load and wash, $^{227}$Ac passes through the cartridge and is eluted in the SW fraction together with $^{223}$Ra, while $^{227}$Th is retained in the first quarter of the cartridge (see FIG. 8). The results show the importance of loading the Ac-containing generator using a high molarity (i.e. 8 M HCl) for separating Ac from Ra.

The invention claimed is:

1. A method for the generation of $^{223}$Ra of pharmaceutically tolerable purity comprising
   i) preparing a generator mixture comprising $^{227}$Ac, $^{227}$Th, and $^{223}$Ra in a first aqueous solution comprising a first mineral acid;
   ii) loading said generator mixture onto a diglycolamide DGA separation medium;
   iii) eluting said $^{223}$Ra from said DGA separation medium using a second mineral acid in a second aqueous solution to give an eluted $^{223}$Ra solution; and
   iv) stripping the DGA separation medium of said $^{227}$Ac and $^{227}$Th by flowing a third mineral acid in a third aqueous solution through the DGA separation medium in a reversed direction, wherein said $^{223}$Ra of pharmaceutically tolerable purity comprises less than 45 Bq $^{227}$Ac per 1 MBq $^{223}$Ra.

2. The method as claimed in claim 1 wherein at least 99.5% of the $^{227}$Ac loaded onto the resin in step ii) is regenerated in step iv).

3. The method as claimed in claim 1 wherein at least 95% of the $^{227}$Th loaded onto the resin in step ii) is regenerated in step iv).

4. The method of claim 1 additionally comprising the step of:
   y) storing said mixture of $^{227}$Ac and $^{227}$Th for a period sufficient to allow ingrowth of $^{223}$Ra by radioactive decay, whereby to re-form a generator mixture comprising $^{227}$Ac, $^{227}$Th, and $^{223}$Ra.

5. The method as claimed in claim 1 wherein the generator mixture has an $^{227}$Ac activity of at least 1 GBq.

6. The method as claimed in claim 1 wherein the generator mixture is stored as a salt and contacted with a separation medium only when separation of $^{223}$Ra is required.

7. The method of claim 6 wherein said contacting occurs for no more than 1 day every 1 to 8 weeks.

8. The method as claimed in claim 1 wherein the DGA separation medium is a DGA resin.

9. The method as claimed in claim 1 wherein the DGA separation medium comprises N,N,N',N'-tetrakis-2-ethylhexyldiglycolamide binding groups.

10. The method as claimed in claim 1 wherein said first mineral acid is an acid selected from the group consisting of $H_2SO_4$, $HNO_3$, and HCl.

11. The method of claim 10 wherein said first mineral acid is HCl.

12. The method as claimed in claim 1 wherein said second mineral acid is an acid selected from the group consisting of $H_2SO_4$, $HNO_3$, and HCl.

13. The method of claim 12 wherein said second acid is HCl.

14. The method as claimed in claim 1 wherein the eluted $^{223}$Ra solution has a contamination level of no more than 45 Bq $^{227}$Ac per 1 MBq $^{223}$Ra.

15. The method as claimed in claim 1 wherein the steps of loading the generator mixture onto the DGA separation medium and eluting the eluted $^{223}$Ra solution provide a separation ratio of $^{223}$Ra to $^{227}$Ac of at least 10,000:1.

16. The method as claimed in claim 1 wherein said third mineral acid is an acid selected from the group consisting of $H_2SO_4$, $HNO_3$, and HCl.

17. The method of claim 16 wherein said third mineral acid is HCl.

* * * * *